United States Patent [19]

Giesecke et al.

[11] 4,310,664

[45] Jan. 12, 1982

[54] PROCESS FOR THE PREPARATION OF PYRIDINE-4-ALDEHYDE PHENYLHYDRAZONES

[75] Inventors: Heinz Giesecke, Leverkusen; Alfred Brack, Odenthal, both of Fed. Rep. of Germany

[73] Assignee: Bayer Aktiengesellschaft, Leverkusen, Fed. Rep. of Germany

[21] Appl. No.: 163,362

[22] Filed: Jun. 26, 1980

[30] Foreign Application Priority Data

Jul. 17, 1979 [DE] Fed. Rep. of Germany ....... 2928746

[51] Int. Cl.$^3$ ................. C07D 213/53; C09B 55/00
[52] U.S. Cl. .................................................. 542/417
[58] Field of Search .................... 546/332; 542/417

[56] References Cited

U.S. PATENT DOCUMENTS

| | | | |
|---|---|---|---|
| 3,274,206 | 9/1966 | Wilbert et al. | 546/332 |
| 3,419,551 | 12/1968 | Komachiya et al. | 542/417 |
| 3,573,287 | 3/1971 | Schorr et al. | 546/332 |
| 4,026,885 | 5/1977 | Frey et al. | 542/417 |
| 4,237,275 | 12/1980 | Bader et al. | 542/417 |

OTHER PUBLICATIONS

Zajac, Jr. et al., J. Org. Chem., 1971, vol. 36(23), pp. 3539–3541.

*Primary Examiner*—Henry R. Jiles
*Assistant Examiner*—Natalia Harkaway
*Attorney, Agent, or Firm*—Sprung, Felfe, Horn, Lynch & Kramer

[57] ABSTRACT

Pyridine-4-aldehyde phenylhydrazones are prepared by catalytic hydrogenation of 4-cyano-pyridine under normal pressure or almost normal pressure in the presence of phenylhydrazine or nuclear-substitution products thereof, in an aqueous medium in the absence of organic solvents, at a pH value between 9 and 12, preferably between 9.5 and 11, and in a temperature range from 0° to 60° C.

5 Claims, No Drawings

PROCESS FOR THE PREPARATION OF PYRIDINE-4-ALDEHYDE PHENYLHYDRAZONES

The present invention relates to a process for the preparation of pyridine-4-aldehyde phenylhydrazones by catalytic hydrogenation of 4-cyano-pyridine under normal pressure or almost normal pressure in the presence of phenylhydrazine or nuclear-substitution products thereof, in an aqueous medium in the absence of organic solvents, at a pH value between 9 and 12, preferably between 9.5 and 11, and in a temperature range from 0° to 60° C. The alkaline reaction is preferably achieved by adding ammonia or other alkaline agents. The process according to the invention is distinguished by its particular simplicity, reliability and profitability. Thus, the use of inflammable or toxic solvents is avoided and no expensive pressure equipment is necessary.

Pyridine-4-aldehyde phenylhydrazone has hitherto been prepared from pyridine-4-aldehyde, which, inter alia, is also accessible by acid hydrolysis of the aldimine obtained by hydrogenation of cyanopyridine. This acid hydrolysis is usually carried out with strong acids, such as sulphuric acid. However, the hydrolysis can also be effected with carbonic acid, under pressure. The present process enables this reaction step to be dispensed with the makes pyridine-4-aldehyde phenylhydrazones accessible not only without intermediate isolation of the sensitive pyridine-4-aldehyde but without intermediate production of this compound at all.

The new process thus represents a considerable simplification of the methods previously known for the preparation of pyridine-4-aldehyde phenylhydrazones, and at the same time overcomes the prejudice evidently existing hitherto that to avoid secondary reactions, the partial hydrogenation of nitriles to the oxidation stage of the aldehyde can be utilised only in combination with the instantaneous acid hydrolysis of the very reactive aldimine.

Possible substituents on the nucleus of the phenylhydrazine are the non-ionic radicals customary in the chemistry of cationic dyestuffs, such as lower alkyl and alkoxy groups and halogen atoms, preferably methyl, ethyl, methoxy, ethoxy, fluorine and chlorine.

Accordingly, examples of suitable phenylhydrazines are, in addition to phenylhydrazine itself, 2-, 3- and 4-methyl-phenylhydrazine, 2-, 3- and 4-methoxy- and -ethoxy-phenylhydrazine, 2-, 3- and 4-chloro-phenylhydrazine, 2,4- and 3,4-dichlorophenylhydrazine and 2,4-dimethoxy- and -diethoxy-phenylhydrazine.

Examples of alkaline agents which can be used are, in addition to ammonia, sodium hydroxide solution, potassium hydroxide solution, milk of lime, sodium carbonate solution and buffer mixtures in the pH range indicated, such as phosphate buffer and borate buffer.

Pyridine-4-aldehyde phenylhydrazones are valuable intermediate products for the preparation of cationic dyestuffs such as are described, for example, in German Pat. No. 1,133,054.

Examples of suitable catalysts are finely divided palladium or platinum, optionally on a suitable support material, and nickel-containing skeleton catalysts, of which Raney nickel is preferred.

EXAMPLE 1

27.8 g of phenylhydrazine hydrochloride are introduced into 200 ml of 25% strength aqueous ammonia solution at room temperature and 20 g of 4-cyano-pyridine are added. After adding 100 ml of 20% strength hydrochloric acid, the mixture is allowed to cool to 25° C., whilst stirring, 4 g of water-moist Raney nickel are added and hydrogenation is carried out in a shaking apparatus at room temperature and under normal pressure until 1.5 times the amount of hydrogen theoretically required has been taken up.

After filtering off the pyridine-4-aldehyde phenylhydrazone/Raney nickel mixture, it is washed with 100 ml of water and filtered off again with good suction. Yield: 30.5 g of a moist mixture of pyridine-4-aldehyde phenylhydrazone and Raney nickel.

56–58% of theory of pure pyridine-4-aldehyde phenylhydrazone are obtained from this mixture by extracting the mixture by stirring with acetone, filtering off the nickel and evaporating the filtrate to dryness.

EXAMPLE 2

43.2 g of ammonium chloride are added to 127 g of 25% strength aqueous ammonia solution, 20.8 g of pheynylhydrazine are then added dropwise at 20° C. and 20.0 g of 4-cyano-pyridine are added to the resulting solution. After adding 4 g of water-moist Raney nickel, hydrogenation is carried out in a shaking apparatus at room temperature and under normal pressure until about 1.3 times the amount of hydrogen theoretically required has been taken up.

A working up procedure of the type in Example 1 gives pyridine-4-aldehyde phenylhydrazone in a comparable yield and purity.

EXAMPLE 3

43.2 g of ammonium chloride are added to 127 g of 25% strength aqueous ammonia solution, and 27.4 g of 4-chloro-phenylhydrazine are added at room temperature. After a further addition of 20.0 g of 4-cyano-pyridine and 4 g of water-moist Raney nickel, hydrogenation is carried out in a shaking apparatus at room temperature and under normal pressure, until about 1.5 times the amount of hydrogen theoretically required has been taken up. After filtering off the catalyst/hydrazone mixture, it is washed with 100 ml of water and filtered off, 200 ml of toluene are added to the moist filter cake and about 80 ml of toluene are distilled off. On cooling the toluene solution which remains, pyridine-4-aldehyde (4-chlorophenyl)-hydrazone precipitates in good yield and purity.

If 4-methyl-phenylhydrazine, 4-ethyl-phenylhydrazine or 4-methoxy-or 4-ethoxy-phenylhydrazine is used instead of 4-chloro-phenylhydrazine and the procedure is otherwise unchanged, the corresponding hydrazones are obtained in similar yield and purity.

We claim:

1. A process for the preparation of a pyridine-4-aldehyde phenylhydrazone which can be substituted on the phenyl nucleus by a non-ionic substituent selected from the group consisting of lower alkyl, lower alkoxy and halogen, which comprises catalytically hydrogenating 4-cyano-pyridine in an aqueous medium at a pH between 9 and 12 in the presence of a phenylhydrazine corresponding to the end-product hydrazone at a temperature of 0° to 60° C. and under normal pressure.

2. A process according to claim 1, wherein the phenyl nucleus is substituted once or twice by a non-ionic substituent selected from the group consisting of methyl, ethyl, methoxy, ethoxy, fluorine and chlorine.

3. A process according to claim 1, wherein the phenyl nucleus is substituted in the 4-position by a non-ionic substituent selected from the group consisting of methyl, methoxy or ethoxy.

4. A process according to claim 1, wherein the phenyl nucleus is unsubstituted.

5. A process according to claim 1, wherein the catalyst is Raney nickel.

* * * * *